United States Patent [19]

Amiet et al.

[11] Patent Number: 4,883,904

[45] Date of Patent: Nov. 28, 1989

[54] PROCESS FOR THE PREPARATION OF ETHYLTRIFLUOROACETOACETATE

[75] Inventors: Louis Amiet; Bernard Langlois, both of Lyons, France

[73] Assignee: Rhone-Poulenc Specialites Chimiques, Courbevoie, France

[21] Appl. No.: 873,509

[22] Filed: Jun. 12, 1986

[30] Foreign Application Priority Data

Jun. 14, 1985 [FR] France .................................. 85 09023

[51] Int. Cl.$^4$ .................. C07C 67/313; C07C 69/716; C07C 67/343
[52] U.S. Cl. .................................... 560/174; 560/183; 562/609; 568/876
[58] Field of Search ........................ 560/174, 184, 183

[56] References Cited

PUBLICATIONS

Filler, R. et al., Tetrahedron, 1963, vol. 19, pp. 879–889, Pergamon Press Ltd. (Northern Ireland).
Bergmann, E. D. et al., J. Chem. Soc., (London), 1959, 3278–3285.

*Primary Examiner*—Vivian Garner
*Attorney, Agent, or Firm*—Finnegan, Henderson, Farabow, Garrett, & Dunner

[57] ABSTRACT

A process for the preparation of ethyltrifluoroacetoacetate is provided. In this first step, ethyltrifluoroacetate is condensed with ethyl acetate in the presence of sodium ethoxide in cyclohexane. In a second step, the condensation product is neutralized with a protonic acid, such as formic acid, to release an enol. In the third step, the ethyltrifluoroacetoacetate obtained is separated by distillation. The ethyltrifluoroacetoacetate is used as an intermediate in syntheses in the pharmaceutical or plant protection industry.

10 Claims, 1 Drawing Sheet

PROCESS FOR THE PREPARATION OF ETHYLTRIFLUOROACETOACETATE

BACKGROUND OF THE INVENTION

The present invention relates to a process for the preparation of ethyltrifluoroacetoacetate and, more particularly, to a process for the preparation of ethyltrifluoroacetoacetate by condensation of ethyltrifluoroacetate and ethyl acetate in the presence of a base.

The condensation of ethyltrifluoroacetate and ethyl acetate in the presence of sodium ethoxide is known, as discussed in Swarts 5 *Bulletin des Sciences academiques du Royaume de Beliqique* (12) 679-725 (1926). The condensation is carried out by refluxing in an anhydrous ether medium and leads to sodium enolate. The enol, which is released with sulfuric acid, comes to equilibrium with its ketonic form. This reaction in a aqueous medium and in the presence of a strong acid results in a partial hydrolysis of the $\beta$-ketoester, which severely reduces the profitability of the process.

It is also known, according to Bayer, Pastor, and Cambon 20 *Journal of Fluorine Chemistry* (1982), to perform the same process as above, but with the sodium ethoxide being replaced by sodium hydride. Although the yields obtained are greater, like the previous process, the use of ether in large quantities and the neutralization with an aqueous mineral acid render this process difficult to use from an industrial point of view because of the need for indispensible safety measures coupled with the low economic profitability.

Some authors, such as Burdon and MacLoughlin 20 *Tetrahedron* 2163-66 (1964), have tried to avoid the use of ether during the condensation of the ethyl esters of trifluoroacetic and acetic acids. However, the phase of enol release is always carried out in an aqueous medium with the use of ether and, hence, these processes cannot be applied on a large scale.

Quite a different reaction technique is described in French Pat. No. 1,310,174. This patent describes the condensation of trifluoroacetic acid chloride with $CH_2=C=O$ followed by an esterification with ethanol. The condensation is carried out at a very low temperature, such as $-30°$ C., in a dichloroethylenebased medium. The trifluoroacetic acid chloride is a gas with a very low boiling point. It is difficult to obtain for industrial use and it is toxic. The ketene $CH_2=C=O$ is also dangerous to use because it is unstable and difficult to transport. Therefore, this process can hardly be considered usable in industry.

SUMMARY OF THE INVENTION

The objective of the present invention is to solve the above problems and provide a safe, effective, economical, and readily usable process of preparing ethyltrifluoroacetoacetate. The present process solves previous safety problems in preparing ethyltrifluoroacetoacetate. The process of the present invention condenses ethyltrifluoroacetate with ethyl acetate in the presence of sodium ethoxide in cyclohexane. The condensation product is neutralized with a protonic acid to release an enol. The ethyltrifluoroacetoacetate is separated by distillation.

The above and other features and advantages of the present invention will be made more apparent from the following description of the preferred embodiment.

BRIEF DESCRIPTION OF THE DRAWING

The accompanying FIG. 1, which is incorporated in and constitutes a part of the specification, illustrates an embodiment of the invention, and, together with the description, serves to explain the principles of the invention.

DETAILED DESCRIPTION OF THE DRAWING

Figure 1:
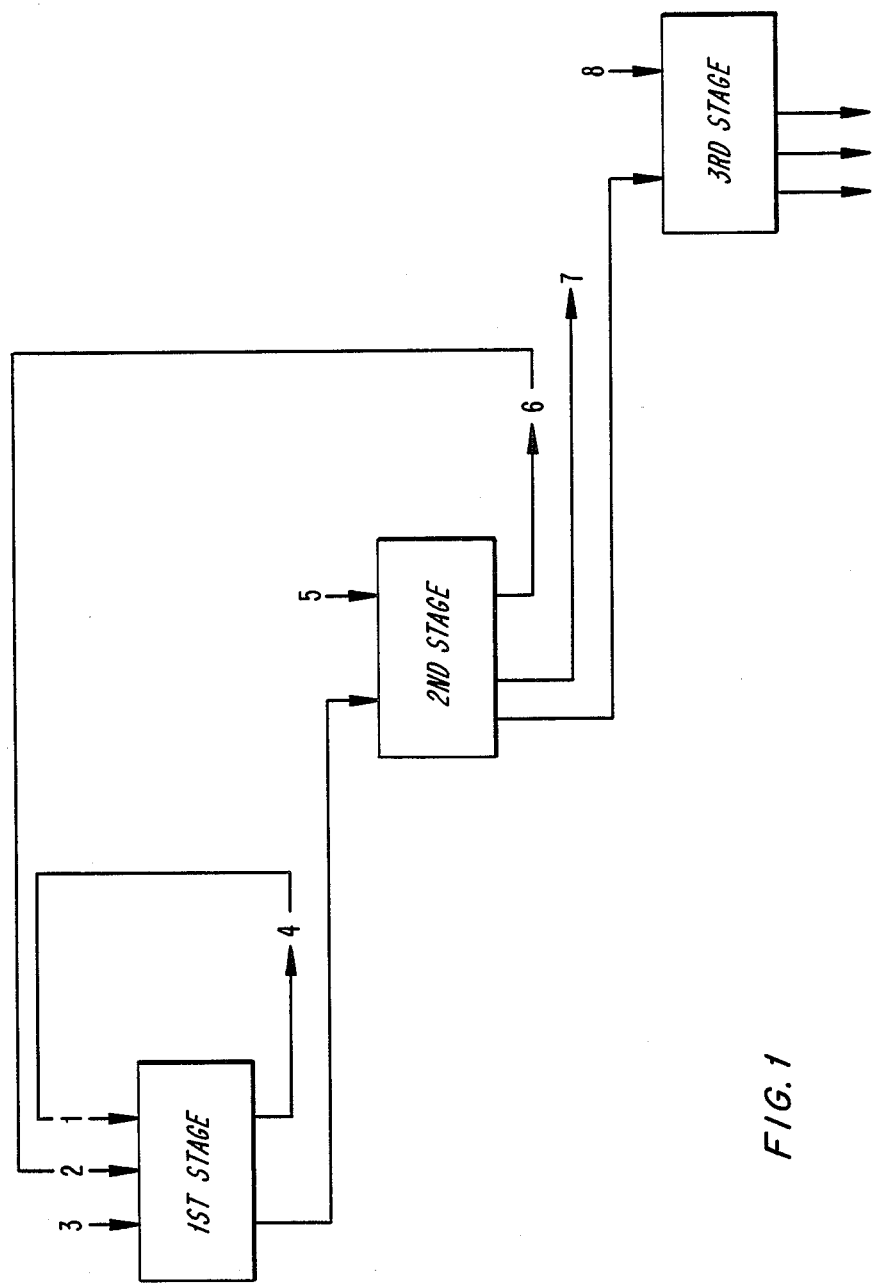
FIG. 1 is a schematic drawing illustrating one embodiment of the process of the present invention.

The present process provides a process for the preparation of ethyltrifluoroacetoacetate. In a first step of the process, ethyltrifluoroacetate and ethyl acetate are condensed in the presence of sodium ethoxide in cyclohexane. As shown in the Figure, ethyltrifluoroacetate (3) and ethyl acetate (2) are condensed in a reactor in the presence of sodium ethoxide (1) in cyclohexane. The sodium ethoxide (1) may be formed in situ by the direct reaction of sodium with ethanol in cyclohexane.

The carrying out of the condensation in an anhydrous medium in cyclohexane makes it possible to avoid the use of diethyl ether. This is particularly advantageous because it is difficult to use diethyl ether in large quantities. The cyclohexane is chemically neutral under the conditions of the reaction and, additionally, it has the advantage of forming an azeotrope with ethanol.

In fact, during the condensation, for each mole of ethyl trifluoroacetoacetate formed, one mole of sodium ethoxide is consumed. Two moles of ethanol are formed according to the reaction:

$$CH_3-COOC_2H_5 + C_2H_5ONa + CF_3COOC_2H_5 \longrightarrow \quad (1)$$

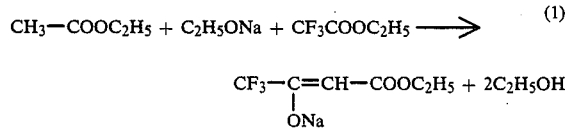

The ethanol is easily removed from the medium by distillation in the form of an azeotrope with cyclohexane (4), which may be an ethanol/cyclohexane azeotrope. This azeotrope may either be brought into contact with metallic sodium to form sodium ethoxide, which will be recycled for reuse in the first step of the process, or be treated in a known manner to extract the alcohol, which can be recycled for reuse in the first step.

In the second step of the process, the condensation product resulting from the first step is neutralized with a protonic acid to release an enol. For example, a sodium salt of the enol of formula (1) is neutralized in an anhydrous medium by a protonic acid to release the enol. This makes it possible to avoid the hydrolysis caused by aqueous strong acids in the prior art. The acid for use in this process should have both an alkaline salt that can be easily precipitated in an organic medium and an acidity greater than that of the enol, but not so high as to degrade the ethyltrifluoroacetoacetate.

A preferred protonic acid for use in the present process is formic acid, which meets all of these conditions. In the embodiment shown in FIG. 1, formic acid (5) is introduced in a solution of ethyl acetate. A preferred composition is a solution having a 30% by weight of formic acid in ethyl acetate.

Preferably, in the second step of the process of the invention, after introducing the formic acid, the ethyl acetate is removed by distillation of an ethyl acetate/cyclohexane azeotrope (6). This azeotrope can easily be recycled for use in the first step of the process.

Additionally, this azeotropic distillation has another important advantage because it facilitates the precipitation of the sodium salt of formic acid. This sodium formate (7) is removed by filtration. The precipitate is rinsed several times with cyclohexane that is then added to the filtrate.

In the third step of the present process, ethyltrifluoroacetoacetate is separated by distillation. In this step, the trifluoroacetoacetate is separated from the ethyl acetate, the ethyltrifluoroacetoacetate, and the remaining cyclohexane. The quantity of ethyl acetate to be separated will be much smaller if, in the course of the second step, prior to the filtration, the azeotropic distillation of the ethyl acetate/cyclohexane has been carried out.

To facilitate the separation of these different constituents, it is particularly advantageous, as shown in the figure, to add a solvent (8) that solubilized the heavy elements that are formed during the reactions. This solvent is to have a boiling point that is greater than that of the ethyltrifluoroacetoacetate. Orthodichlorobenzene meets all of these demands.

Preferably, in the first step, a molar ratio of ethyltrifluoroacetate to sodium ethoxide that is less than or equal to 1 and a molar ratio of ethyl acetate to ethyltrifluoroacetate of between 1 and 2 and, preferably of between 1.5 and 2, are used. In the second step of the present process, it is preferred to use a molar ratio of formic acid to sodium ethoxide of approximately 1.

The ethyltrifluoroacetoacetate produced by the process of the present invention can be used as an intermediate in syntheses in the pharmaceutical or the plant protection industry. For example, see U.S. Pat. Nos. 4,251,261 and 3,953,453.

The invention will be described more completely by means of the following examples which should not be regarded as limiting the invention.

EXAMPLE 1

Sodium ethylate is prepared in a known manner using 9.56 moles (220 g) of metallic Na and 5.180 g of absolute EtOH in a 10-liter flask connected to an Oldershaw type 20-plate glass distillation column that is placed n a dry nitrogen atmosphere.

After the complete reaction of Na, cyclohexane loads are introduced by distilling each time an alcohol/cyclohexane azeotrope until the temperature at the top substantially reaches the boiling point of pure cyclohexane, which is 80-81° C. Thus, 17.6 liters of cyclohexane are introduced into the reaction and 21.8 liters of the azeotrope (16.7 kg) are recovered.

The reaction medium is cooled and 9.56 moles (1,358 g) of pure ethyltrifluoroacetate are then introduced in the course of 4 hours with stirring.

19.12 moles of pure anhydrous ethyl acetate (1,687 g) are then introduced into the medium at 50° C. over the course of 4 hours 30 minutes. 3 liters of cyclohexane are then added to the reaction and the following fractions are distilled at atmospheric pressure:

first of all, a 2,822 g fraction containing 27% of EtOH, 14% of AcOEt (ethylacetate), 1.25% of ethyltrifluoroacetate, and 57% of cyclohexane distilling at 64° C. to 69° C.;

then, a 1,181 g fraction distilling until 77° C. The composition of the recovered fraction contained 3.83% EtOH, 13.4% of AcOEt, and 82.8% of cyclohexane (analysis by gas chromatography).

Two liters of cyclohexane are loaded again and a mixture of 440 g of pure HCOOH (9.56 moles) and 1.026 g of AcOEt are then poured, with stirring, at 40° C. The time of duration is 1 hour 30 minutes.

The reaction mixture is allowed to cool with gentle stirring. Filtration is then carried out in a Buchner funnel that is fitted with a filtering cloth. The precipitate is then rinsed once with 1 liter of cyclohexane, then a second time with 0.75 liters of cyclohexane.

The filtrate with the cyclohexane rinsing are then subjected to distillation. The following fractions are distilled in sequence:

(1) at atmospheric pressure, the first fraction distilled at a temperature of 35° C. and contained: an AcOEt/cyclohexane mixture having some traces of alcohol; followed by, under reduced pressured at 140 mm Hg, almost pure cyclohexane (99.5%); and then a 110 g intermediate fraction containing 75.5% of ETFAA (ethyltrifluoroacetoacetate);

(2) under reduced pressure at 80 mm Hg, distilling until 66° C. a 1,197 g mass constituting the main fraction;

(3) finally, when the pressure is reduced further to approximately 55 mm Hg and the temperature in the still at the end of the distillation reaches 142° C., a distillate mass of 103 g is recovered. There remains a 165 g residue of tarry appearance, which becomes very viscous (waxy) on cooling.

The three last fractions distilled, totalling 1,410 g, are combined and this liquid is subjected to a further refinement with a 20-plate column at a pressure of 140 mm Hg. Before a steady temperature of 82° C. to 83° C. is reached at the head of the column, a 32 g mass is separated. Then, at 82/83° C., a 1.314 g mass of 99.1% pure ETFAA, as analyzed by gas chromatography, is collected.

A residue of approximately 58 g is left behind.

EXAMPLE 2

Solid sodium ethylate, obtained under the mark Dynamit Nobel, is used directly. Into the same apparatus as before, 1,700 g of cyclohexane are introduced followed with gentle stirring, under neutral atmosphere (nitrogen), of 656 g of solid technical grade ethylate. Then, as in the previous example, ethyltrifluoroacetate followed by ethyl acetate are added in the same way using the same quantities. The procedure is continued in the same manner as in the previous example up to the filtration of sodium formate and the rinsing of the cake on the filter.

625 g of orthodichlorobenzene are then added to the liquid obtained, before subjecting it to distillation.

After the sequential separations of the binary AcOET/cyclohexane, followed by the remaining cyclohexane under reduced pressure at 140 mm Hg, a 1.321 g mass containing 98.8% of ethyltrifluoroacetoacetate, as analyzed by gas chromatography, is distilled at first at this pressure, and then with pressure reduced to 95 mm Hg. At the end of the distillation, the temperature in the still does not exceed 115° C. The liquid residue weighing 780 g is easily poured out on cooling.

While particular embodiments of the invention have been described, it will be understood that the invention is not so limited since many modifications and variations could be made without departing from the spirit or scope of the invention.

What is claimed is:

1. A process for the preparation of ethyltrifluoroacetoacetate comprising the steps of:
   (a) condensing ethyltrifluoroacetate and ethyl acetate in the presence of sodium ethoxide in an anhydrous medium in cyclohexane;
   (b) neutralizing the condensation product in an anhydrous medium with a protonic acid to release an enol; and
   (c) separating by distillation the ethyltrifluoroacetoacetate obtained.

2. The process according to claim 1, wherein sodium ethoxide is formed in situ by the reaction of metallic sodium with ethanol.

3. The process according to claim 1, wherein, ortho-dichlorobenzene is added prior to distillation.

4. The process according to claim 1, wherein in step (b) the protonic acid is formic acid.

5. The process according to claim 4, wherein the formic acid is used in a solution with ethyl acetate.

6. The process according to claim 4, wherein sodium formate formed during step (b) is removed by filtration.

7. The process according to claim 6, wherein before filtration, ethyl acetate is removed by distillation of an azeotrope with cyclohexane.

8. The process according to claim 1, wherein in step (a) after the condensation of ethyltrifluoroacetate and ethyl acetate, the ethanol released is distilled in the form of an azeotrope with cyclohexane.

9. The process according to claim 8, wherein the ethanol/cyclohexane azeotrope is recycled for use in step (a).

10. The process according to claim 1, wherein in step (b), after neutralization the ethyl acetate is removed by distillation of an ethyl acetate/cyclohexane azeotrope, said azeotrope being recycled for use in step (a).

* * * * *